(12) United States Patent
Hiraoka

(10) Patent No.: US 8,253,793 B2
(45) Date of Patent: Aug. 28, 2012

(54) LUMBER INSPECTION METHOD, DEVICE AND PROGRAM

(75) Inventor: Noriyuki Hiraoka, Aichi (JP)

(73) Assignee: Meinan Machinery Works, Inc., Aichi (JP)

( * ) Notice: Subject to any disclaimer, the term of this patent is extended or adjusted under 35 U.S.C. 154(b) by 496 days.

(21) Appl. No.: 12/596,211

(22) PCT Filed: Apr. 20, 2007

(86) PCT No.: PCT/JP2007/058583
§ 371 (c)(1),
(2), (4) Date: Oct. 16, 2009

(87) PCT Pub. No.: WO2008/136067
PCT Pub. Date: Nov. 13, 2008

(65) Prior Publication Data
US 2010/0141754 A1 Jun. 10, 2010

(51) Int. Cl.
*H04N 7/18* (2006.01)
*G06F 15/16* (2006.01)

(52) U.S. Cl. .......................................... 348/92; 348/91
(58) Field of Classification Search ................ 348/91–93
See application file for complete search history.

(56) References Cited

U.S. PATENT DOCUMENTS

| | | | |
|---|---|---|---|
| 4,827,142 A | 5/1989 | Hatje | |
| 4,992,949 A * | 2/1991 | Arden | 700/223 |
| 5,357,112 A * | 10/1994 | Steele et al. | 250/340 |
| 5,544,256 A * | 8/1996 | Brecher et al. | 382/149 |
| 5,960,104 A * | 9/1999 | Conners et al. | 382/141 |
| 6,072,890 A * | 6/2000 | Savard et al. | 382/110 |
| 2006/0262972 A1* | 11/2006 | Hiraoka | 382/141 |

FOREIGN PATENT DOCUMENTS

| | | |
|---|---|---|
| JP | 62-192623 | 8/1987 |
| JP | 08-145914 | 6/1996 |
| JP | 09-210785 | 8/1997 |
| JP | 09-210785 A | 8/1997 |
| JP | 2001-216585 A | 8/2001 |
| JP | 2002-286549 A | 10/2002 |
| JP | 2004-109018 A | 4/2004 |
| JP | 2004-301574 A | 10/2004 |
| JP | 2006-322774 | 11/2006 |
| JP | 2007-040913 | 2/2007 |
| JP | 2007-147442 | 6/2007 |

OTHER PUBLICATIONS

Cao Lin and Jiang Xian, "Study on Blue-Staining Chinese White Poplar Bleached Technique", Scientia Silvae Sincae, vol. 42, No. 3, Mar. 31, 2006.

* cited by examiner

*Primary Examiner* — Zarni Maung
(74) *Attorney, Agent, or Firm* — McGlew and Tuttle, P.C.

(57) ABSTRACT

An imaging means captures a color image of lumber. An image processing means obtains the color distribution of the color image captured by the imaging means, compares the obtained color distribution with a predetermined color distribution of normal lumber, judges the obtained color distribution as an abnormal one when it is deviated from the color distribution of normal lumber by a predetermined value or more, and detects a defect of the lumber having the abnormal color distribution deviated by a value larger than the predetermined value in an area on the surface of the lumber captured by the imaging means.

11 Claims, 7 Drawing Sheets

LUMBER INSPECTION METHOD, DEVICE AND PROGRAM

CROSS-REFERENCE TO RELATED APPLICATION

This application is based upon and claims the benefit of priority of the prior International application PCT/JP2007/058583, filed on Apr. 20, 2007, the entire contents of which are incorporated herein by reference.

BACKGROUND OF THE INVENTION

1. Field of the Invention

The present invention relates to a lumber inspection method and device thereof for detecting defective portions due to discoloration which exist in wood-based material such as a veneer or a cut piece cut from a log of wood or the like. For example, for manufacturing plywood, a log is cut using a cutting tool to consecutively obtain veneers with a thickness of several millimeters. The veneers are then cut to a predetermined size, and after drying, several veneers are integrated through lamination using an adhesive. During such manufacturing processes, it is necessary to sort the veneers into those that will compose the outer layers of plywood or, in other words, those with little or no aesthetic defects, and those that will compose the inner layers or, in other words, those with many, albeit nonproblematic, aesthetic defects according to the degrees of positions, numbers, dimensions or the like of defects that affect the quality of the veneer (such as imperfections due to surface discoloration of lumber, warping, holes formed by knots in the veneer having fallen out, and cracks). Such sorting involves classifying into, for example, five to seven grades.

2. Description of the Related Art

Conventionally, the process of sorting veneers into those that will form surface layers of plywood and those that will form inner layers thereof involves naked eye determination by a worker on veneers conveyed through a conveyer.

In addition, a conventional inspection method of defective portions in lumber involves capturing an image of lumber with a color CCD camera, comparing a video signal against reference colors of pitch and discolorations using a color image extraction device and binarizing the video signal, labeling a binarized image matching a measurement object region and contrasting the binarized image with a tolerance value in order to detect defective sites including attached resin such as pitch, rot, and discoloration (refer to Patent Document 1).

Patent Document 1: Japanese Patent Laid-Open No. 09-210785

The conventional techniques described above contain the following problems.

Naked eye determination is inaccurate due to inconsistencies in judgment from person to person and is low in productivity because conveyor speed cannot be increased.

In addition, the conventional method of inspecting defective portions in lumber which involves comparing with a reference color and performing binarization does not include accurate defect inspection using color distribution.

It is an object of the present invention to solve such problems in the prior art and to enable accurate detection of defective portions due to lumber surface discoloration that affect lumber quality using color distribution from a captured image of lumber such as a veneer captured by imaging means even when changes occur in the chromaticity, brightness, and the like of an abnormal portion.

SUMMARY

An aspect of the present invention provides a lumber inspection method executed by a programmed processor, the method comprises: obtaining a color image of lumber captured by imaging means; obtaining a color distribution of the color image captured by the imaging means; comparing the obtained color distribution with a predetermined color distribution of normal lumber; judging the obtained color distribution as an abnormal one when it is deviated from the color distribution of normal lumber by a predetermined value or more; and detecting an area on the surface of the lumber captured by the imaging means whose abnormal color distribution has a value greater than the predetermined value as a defect of the lumber.

Another aspect of the invention provides a lumber inspection device, which comprises: an imaging unit for capturing a color image of lumber; and an image processing unit for obtaining a color distribution of the color image captured by the imaging unit, comparing the obtained color distribution with a predetermined color distribution of normal lumber, judging the obtained color distribution as an abnormal one when it is deviated from the color distribution of normal lumber by a predetermined value or more, and detecting an area on the surface of the lumber captured by the imaging unit whose abnormal color distribution has a value greater than the predetermined value as a defect of the lumber.

DESCRIPTION OF THE PREFERRED EMBODIMENT

Figure 1:
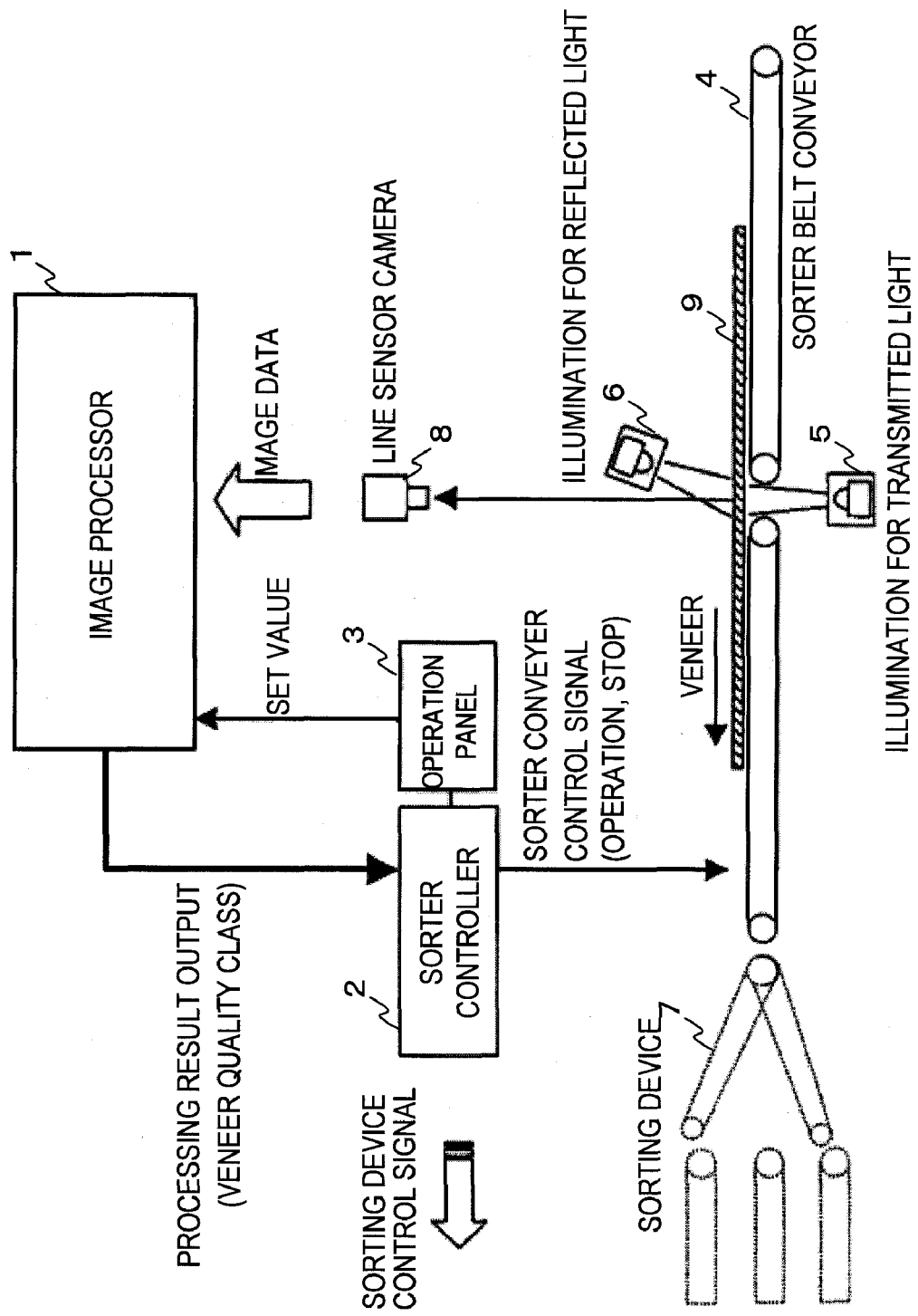
FIG. 1 is an explanatory diagram of a veneer sorter according to the present invention.

FIG. 1 is an explanatory diagram of a veneer sorter. In FIG. 1, reference numeral 1 denotes an image processor (image processing means), 2 denotes a sorter controller, 3 denotes an operation panel, 4 denotes a belt conveyor, 5 denotes an illumination for transmitted light, 6 denotes an illumination for reflected light, 7 denotes a sorting device, 8 denotes a line sensor camera (imaging means), and 9 denotes a veneer (lumber).

In order to solve the problems described above, one aspect of the present invention is configured as follows.

(1) Imaging means 8 captures a color image of lumber 9. Image processing means 1 obtains a color distribution of the color image captured by the imaging means 8, compares the obtained color distribution with a predetermined color distribution of normal lumber, judges the obtained color distribution as an abnormal one when it is deviated from the color distribution of normal lumber by a predetermined value or more, and detects an area on the surface of the lumber captured by the imaging means 8 whose abnormal color distribution has a value greater than the predetermined value as a defect of the lumber. Therefore, defective portions due to discoloration of the lumber surface which affect lumber quality can be accurately detected using color distribution.

(2) In the lumber inspection method or device according to (1) described above, when setting, as an inspection object, lumber whose defective area is small relative to an inspection object area, image distributions acquired on a per-inspection object basis are replaceably used from case to case as the predetermined color distributions of normal lumber. Consequently, predetermined color distributions of normal lumber can be readily acquired.

(3) In the lumber inspection method or device according to (1) or (2) described above, an abnormal brightness portion is detected by obtaining a brightness histogram of the color distribution of the captured color image. Consequently, an abnormal brightness portion such as a burn can be readily detected.

(4) In the lumber inspection method or device according to (3) described above, the entire brightness histogram of the predetermined color distribution of normal lumber is assumed so as to follow a normal distribution, and an entire normal distribution is estimated from a cumulative frequency of a partial region. Consequently, a color distribution of normal lumber can be estimated from lumber to be inspected without having to determine, in advance, a color distribution of normal lumber.

(1) Description of Veneer Sorter

FIG. 1 is an explanatory diagram of a veneer sorter. FIG. 1 shows an entire configuration of the veneer sorter. The veneer sorter includes an image processor 1, a sorter controller 2, an operation panel 3, a belt conveyor 4, an illumination for transmitted light 5, an illumination for reflected light 6, a sorting device 7, and a line sensor camera 8.

The image processor 1 processes image data from the line sensor camera 8 and outputs processing results such as a veneer quality class to the sorter controller 2. The sorter controller 2 outputs sorter conveyor control signals such as for operating and stopping the conveyor, as well as control signals for the sorting device 7, in response to output from the image processor 1. The operation panel 3 is an operation panel for performing operations such as changing the set values of the image processor 1 and controlling of the sorter controller 2. The belt conveyor 4 conveys a veneer 9. The illumination for transmitted light 5 is illuminating means (light source) such as an LED for detecting holes, cracks, and the like in the veneer 9, and an illumination that differs in color (e.g., a green illumination) from the illumination for reflected light 6 is used. This is done in order to distinguish (by color and intensity) transmitted light from reflected light from the illumination for reflected light 6 to detect holes (knot holes), cracks, and the like in a veneer. The illumination for reflected light 6 is illuminating means (light source) such as an LED for detecting light reflected off of the veneer 9 and a white illumination is normally used. The line sensor camera 8 captures line images of the veneer 9.

An operation of the veneer sorter involves capturing an image of the veneer 9 conveyed by the belt conveyor 4 with the line sensor camera 8, and outputting image data to the image processor 1. The image processor 1 processes the image data, and outputs processing results such as a veneer quality class to the sorter controller 2. The sorter controller 2 outputs a control signal to the sorting device 7 and sorts the veneer 9 according to class. Sorting is performed according to the degree of the numbers of wormholes, holes or fallen knots, live knots, dead knots, wanes, cracks, pitch and bark pockets, blue stains, warp (warpage value) and the like, as well as their respective sizes (dimensions).

(2) Description of Image Processor

Figure 2:
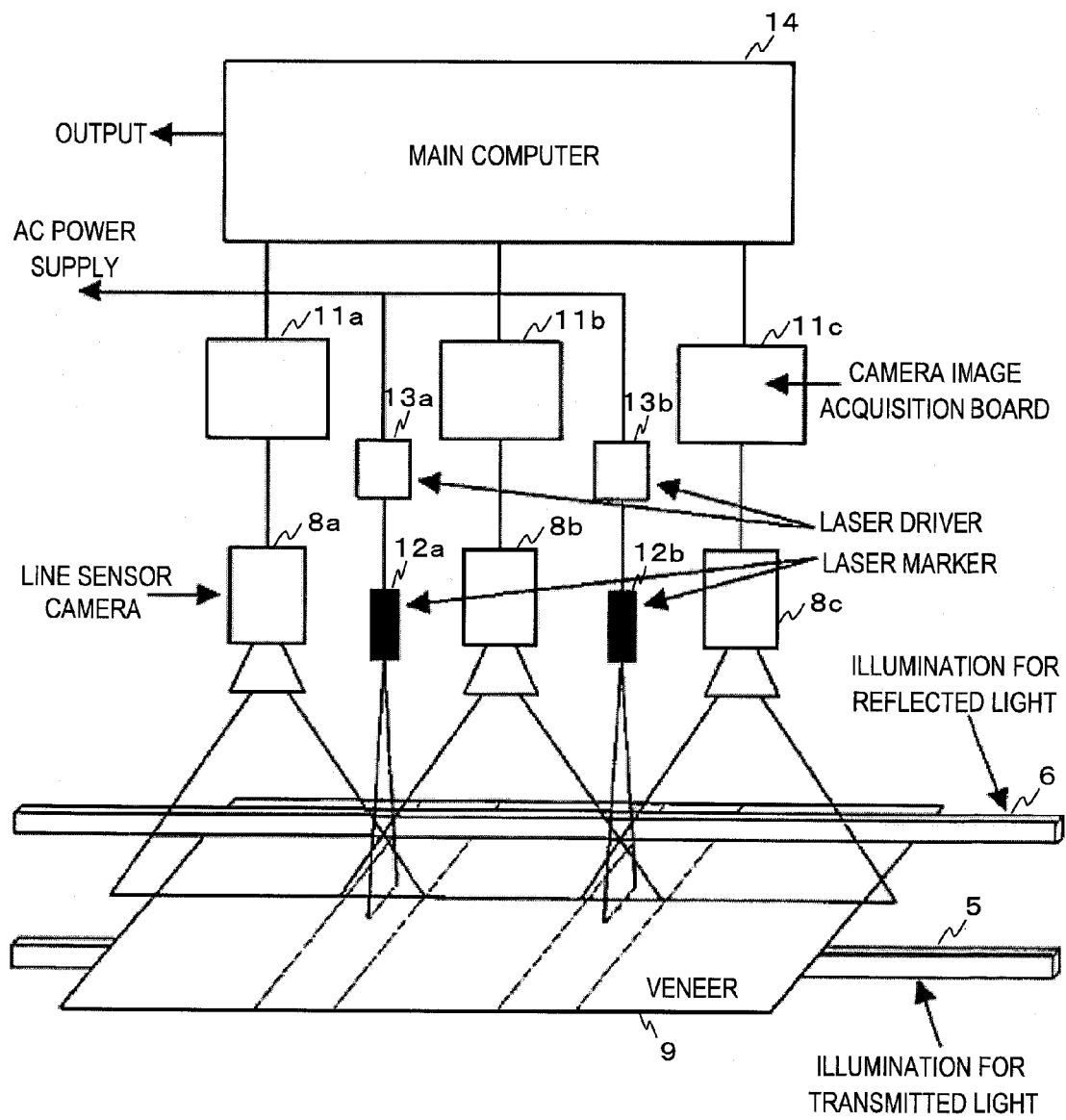
FIG. 2 is an explanatory diagram of an image processor according to the present invention.

FIG. 2 is an explanatory diagram of the image processor 1. In FIG. 2, the image processor 1 includes: three line sensor cameras 8a, 8b, and 8c; camera image acquisition boards 11a, 11b, and 11c; laser markers 12a and 12b; laser drivers 13a and 13b; and a main computer 14.

The line sensor cameras 8a, 8b, and 8c divide the veneer 9 in a direction perpendicular to the conveying direction among the three cameras and capture color images. The camera image acquisition boards 11a, 11b, and 11c perform digitalization every time a single line image is loaded from the respective line sensor cameras, and delivers image data to the main computer 14. The laser markers 12a and 12b irradiate thin light beams in the conveying direction of the veneer which are to be used as marks when synthesizing (coupling) the respective images from the line sensor cameras 8a, 8b, and 8c. The irradiated light beam can be a thin light beam of a different color (for example, a red laser monochromatic light beam) from the color of the veneer (lumber) so as to be readily removable in subsequent processes. The laser drivers 13a and 13b are connected to an AC power supply and drive the laser markers 12a and 12b. The main computer 14 includes processing means, storing means, output means, and the like and performs image processing (image synthesis, knot searching, defect searching, and the like) on the veneer 9. In this case, the camera image acquisition boards 11a, 11b, and 11c and the main computer 14 make up the image processing means.

An operation of the image processor involves illuminating the conveyed veneer 9 with light from the illumination for transmitted light 5 and the illumination for reflected light 6. Every time a single line image is loaded from the line sensor cameras 8a, 8b, and 8c, the camera image acquisition boards 11a, 11b, and 11c deliver data thereof to the main computer 14. The main computer 14 performs compensation on received images and detects warpage values, and sequentially couples the images. Eventually, by the time the image acquisition boards 11a, 11b, and 11c finish loading images, the main computer 14 nearly finishes color image synthesis and black-and-white grayscale image conversion. Subsequently, the main computer 14 couples images from the camera image acquisition boards 11a, 11b, and 11c in which an image of the veneer is divided into three parts.

At this point, laser marks are irradiated to the veneer 9 from the laser markers 12a and 12b to divide the veneer 9 into three parts. Furthermore, by having the line sensor cameras 8a, 8b, and 8c align line images to the respective laser marks on the veneer 9, images can be readily coupled. Additionally, in order to increase image processing speed, knot searching can be performed using black-and-white grayscale images which have a large number of pixels, while searching for dead knots and the like can be performed using scaled-down (with reduced number of pixels) color images.

The operation of the image processor will now be described in two stages, namely processing during image capturing, and processing thereafter.

<Description of Processing During Image Capturing>

Image data captured by the line sensor cameras 8*a*, 8*b* and 8*c* is delivered per line to the main computer 14 and is synthesized as a single entire image.

The camera image acquisition boards 11*a*, 11*b*, and 11*c* load a single line color image from the line sensor cameras 8*a*, 8*b*, and 8*c*, detect a position of a laser mark (coupling position), and sends the single line color image together with information on the laser mark position to the main computer 14.

The main computer 14 performs compensation on the arrived single line color image and concurrently detects a "warpage value", and performs synthesis based on the aforementioned position information (laser mark). At this point, if warpage exists in the inspection object, a detection trajectory at the position of the laser mark becomes nonlinearly distorted, whereby a warpage value can be detected from the amount of distortion.

At the stage where image capturing by the camera image acquisition boards 11*a*, 11*b*, and 11*c* is completed and the last single line color image is received, the main computer 14 completes synthesis of an entire color image. In addition, in order to efficiently utilize the time during image capturing, processing performable for each single line such as black and white conversion and reduction can be performed concurrently.

<Description of Processing During Image Analysis after Image Capturing>

The camera image acquisition boards 11*a*, 11*b*, and 11*c* stand by until the arrival of the next board (veneer) is detected.

Based on preset information such as the size, type, or the like of the board to become the inspection object, the main computer 14 performs knot searching, defect detection using transmitted light, and the like according to an area to be calculated and to set values, and eventually performs sorting so as to also include a warpage value. The results thereof are displayed on a display, not shown, and are also outputted to the sorter controller 2.

While a description has been given above on a case where computers (PCs) are used as the camera image acquisition boards 11*a*, 11*b*, and 11*c*, the main computer 14, and the like in the image processor, the number of computers to be used may be altered depending on the amount of image data, computer processing speeds, or the like. Alternatively, processing can be performed by a single computer.

In addition, while a case has been described in which three line sensor cameras 8*a*, 8*b*, and 8*c* are used, one, two, or four or more line sensor cameras can be alternatively used depending on the size and type of the board to become an inspection object, computer processing performance, or the like.

(3) Description of Detection of Defective Portion Due to Veneer Surface Discoloration Defective portions due to discoloration of the lumber surface which affect lumber quality can be detected using means and according to the method described below.

A defective portion due to discoloration refers to a discolored portion caused by fungi or the like entering lumber from the outside or, in the case of a veneer used in plywood or the like, a burn caused by a kiln, a trace of the bark of lumber, pitch formed inside lumber rising up to the surface thereof, and the like.

It is now possible to detect such portions as defective portions.

(Description of Defective Portion Detecting Means)

1) An image of the lumber surface is captured by color line sensor cameras 8*a*, 8*b*, and 8*c*, and the image is loaded into a computer using an input device (input means).

2) The captured image is saved as a color image in which each pixel is made up of RGB (red, green, and blue) in a computer memory (storage means).

3) A computer image processing program (image processor) converts the RGB image into an HSV (hue, saturation, and brightness) image.

4) A defective portion is detected from the HSV by the method described below.

(Description of Defective Portion Detecting Method)

The surface color of normal (healthy) lumber of the same species is more or less distributed across a specific saturation and hue area regardless of whether the color is dark or light. However, a defective portion such as fungi deviates from a healthy color distribution in both saturation and hue due to the difference in substance. In addition, a defective portion such as a burn is distributed across a portion much darker (lower in brightness) compared to a healthy color distribution.

Therefore, the method features finding out the deviation of saturation and hue and the deviation of brightness of a color distribution of an inspection object lumber surface in comparison to the color distribution of a healthy lumber surface, and detecting a portion with a significant deviation value as a defective portion.

(4) Description of Method of Acquiring a Color Distribution of a Healthy Lumber Surface to be Used as a Reference 1) For an inspection object species, an image of the surface of healthy lumber is captured by a color line sensor camera.

2) In step 1), in order to ensure sufficient statistical accuracy, a plurality of (around 20 or more) images of the surface in different conditions is taken for the same species.

3) Each pixel color in all of the images described above is positioned in a three-dimensional color place on the computer memory to create a three-dimensional color distribution.

As for the three-dimensional color space, an RGB (red, green, and blue) color place, an HSV (hue, saturation, and brightness) color space, an Lab (where "L" denotes brightness, "a" denotes a hue element ranging from green to red, and "b" denotes a hue element ranging from blue to yellow), or the like can be used.

4) A two-dimensional distribution is obtained for each equal brightness plane in the three-dimensional color distribution to acquire a point indicating a greatest frequency.

5) By varying the brightness in stages, a curve approximately connecting the greatest frequency points in 4) above can be acquired. The curve shall be referred to as a reference central axis of the three-dimensional color distribution.

For example, when the value of brightness ranges from 0.0 to 1.0 in an HSV color distribution, a two-dimensional color distribution of the hue and saturation of pixels having an equal brightness value is obtained for each 0.02 brightness segment, and a curve connecting greatest frequency points thereof is acquired and set as the reference central axis of the three-dimensional color distribution. At the same time, a standard deviation σc(v) of the two-dimensional distribution of hue and saturation is obtained.

6) When it is known in advance that a defective portion area is small relative to the inspection object area, the reference distribution can be replaced with an image distribution acquired for each inspection object. This is because only an average of a distribution of a healthy portion and a standard deviation value need be obtained.

(5) Description of Defect Inspection Method

1) An image of an inspection object lumber surface is captured by a color line sensor camera.

2) Each pixel in the image is positioned in a three-dimensional color space to create a three-dimensional color distribution.

3) A chromatic deviation from the reference central axis of the three-dimensional color distribution is obtained as follows.

Figure 3:
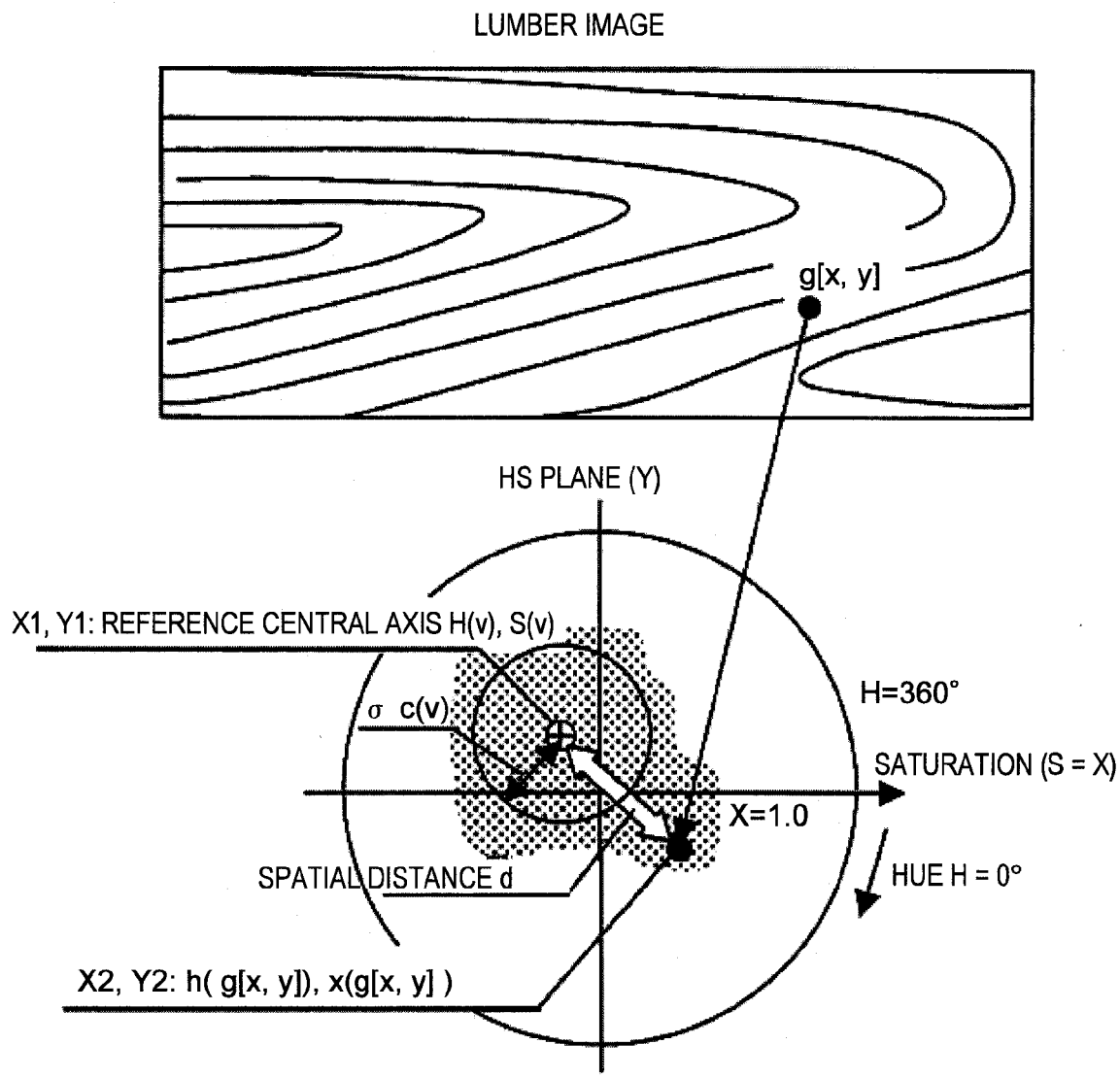
FIG. 3 is an explanatory diagram showing conversion of colors of respective points of an image g onto an HS plane, according to the present invention.

For example, if a pixel at a position x, y in the object image is denoted by g[x, y], a color in the HSV color distribution space is expressed by hue value: $h(g[x,y])$, saturation value: $s(g[x,y])$, brightness value: $v(g[x,y])$, reference central axis coordinates at a specific brightness v on the reference central axis of the three-dimensional color distribution obtained earlier is expressed by hue value: $H(v)$, saturation value: $S(v)$, and the abscissa and the ordinate of the equal brightness plane are denoted as X and Y, respectively, then we arrive at FIG. 3. FIG. 3 is an explanatory diagram showing conversion of colors of respective points of an image g onto an HS plane. In FIG. 3, the pixel g[x, y] of the lumber of the object image is converted into Cartesian coordinates X2, Y2 on the HS plane. While a color distribution (refer to hatching) may take various shapes other than a circle, an approximate circle is obtained at standard deviation.

Here, Cartesian coordinates X1, Y1 of reference central axis coordinates H(v), S(v) may be expressed as $X1=S(v)\cdot\cos(2\pi\cdot H(v)/360)$, $Y1=S(v)\cdot\sin(2\pi\cdot H(v)/360)$.

Cartesian coordinates X2, Y2 of the pixel g[x, y] may be expressed as $X2=S(v)\cdot\cos(2\pi\cdot h(v)/360)$, $Y2=S(v)\cdot\sin(2\pi\cdot h(v)/360)$.

A square spatial distance d from the reference central axis can be obtained as $d^2=(X1-X2)^2+(Y1-Y2)^2$.

Thus, a chromatic deviation value Zc[x, y] can be expressed as $Zc[x,y]=(\sqrt{d})/(\sigma c(v)\times\beta c)$, where σc(v) denotes a standard deviation of a hue and saturation two-dimensional color distribution at a brightness v of the reference central axis, and βc denotes a coefficient for determining how far a color must be separated from the reference central axis to be assumed abnormal in factors of σc(v) which takes a value of, for example, around 1.0 to 2.0.

In addition, a spatial distance deviation can be similarly obtained using other color distributions such as an Lab color space.

4) Next, in order to calculate an actual area of a defective portion, only color pixels deviated from standard in the color distribution space whose original lumber pixel g[x, y] locally forms a cluster must be selected. In doing so, a method referred to as relaxation that is a general image processing technique can be used to remove discontinuous isolated points and enhance portions with significant deviation while taking the colors of surrounding pixels into consideration.

Figure 4:
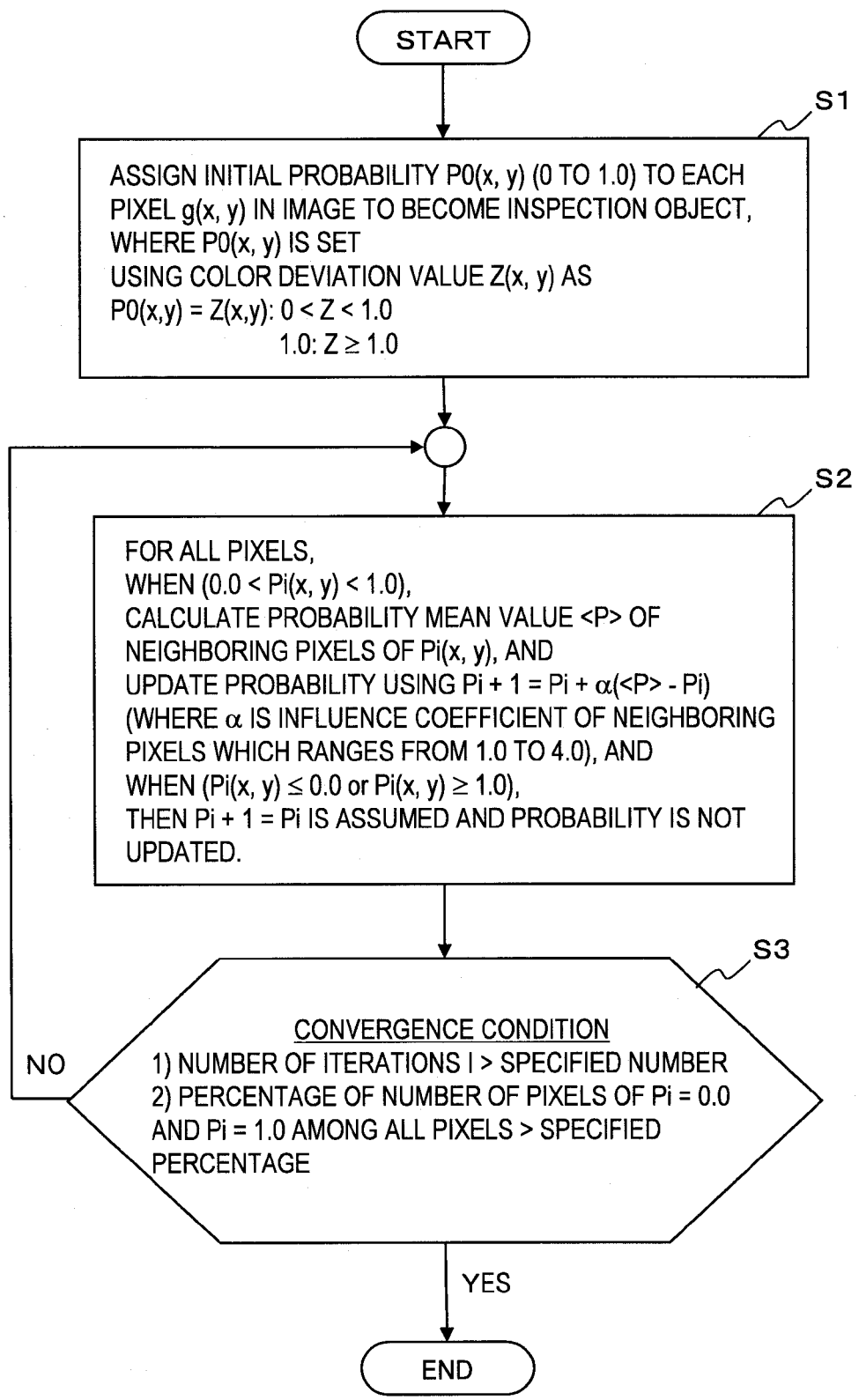
FIG. 4 is an explanatory diagram of relaxation according to the present invention.

As an example, a defective area due to abnormal chromaticity can be determined by relaxation that uses a chromatic deviation value Zc[x, y] from the reference central axis as an initial label (refer to the description of FIG. 4).

(Description of Defective Portion Detection by Abnormal Brightness)

5) A histogram in the reference central axis (brightness axis) direction of the three-dimensional color distribution is obtained.

6) If the brightness histogram of the healthy portion described above is a normal distribution (Gaussian distribution) with a mean value of Vm and a standard deviation of σv, then a brightness deviation value Zv[x, y] may be obtained as $Zv[x,y]=|Vm-g[x,y]\cdot v|/(\sigma v\times\beta v)$, where βv denotes a coefficient for determining how far a color must be separated from the brightness mean value Vm to be assumed abnormal in factors of σv which takes a value of, for example, around 1.0 to 4.0.

A total deviation value Zt[x, y] of chromaticity and brightness may be expressed as $Zt[x,y]=Zc[x,y]+Zv[x,y]$.

When the brightness histogram does not form a normal distribution due to camera characteristics or the like (for example, when saturation occurs at a bright portion close to 1.0 brightness), the mean value Vm and the standard deviation σv may not necessarily be calculated accurately. In such a case, assuming that the histogram follows a standard normal distribution, a normalized cumulative probability distribution function F(x) can be expressed as $$F(x) = \int f(x)dx \qquad \text{[Expression 1]}$$
$$= \frac{1}{\sqrt{(2\pi\sigma^2)}} \int \exp\left\{-\frac{(x-\mu)^2}{2\sigma^2}\right\}dx$$

(where x denotes brightness, μ denotes a mean value of brightness, and σ denotes standard deviation.)

Brightness histograms are integrated starting at the lowest brightness, and brightnesses for which a value (cumulative frequency) obtained by dividing the integrated value by the total number of pixels and corresponding to p1, p2, p3, and p4 below are respectively obtained and are to be denoted as V1, V2, V3, and Vm.

Figure 8:
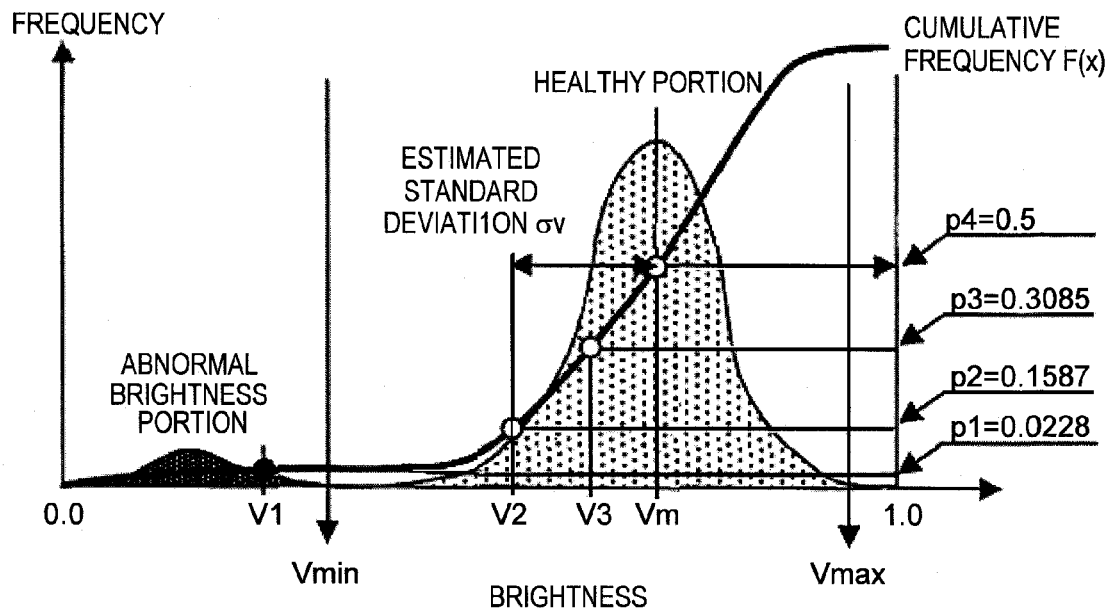
FIG. 8 is an explanatory diagram of a pixel distribution (normal distribution profile) in a central axis direction according to the present invention.

$p1=F(\mu-2.0\sigma)=0.0228$ $p2=F(\mu-1.0\sigma)=0.1587$ $p3=F(\mu-0.5\sigma)=0.3085$ $p4=F(\mu)=0.5$ In addition, valid regions Vmin and Vmax attainable by V1, V2, V3, and Vm can be empirically obtained from lumber or the like to be used as reference. For example, a possible setting can be Vmin=0.25, Vmax=0.9.

a) If a brightness position corresponding to V2:F(Vm−σ)=0.1587 and Vm:F(Vm)=0.5 existing in the valid region can be found among V1, V2, V3, and Vm, then an estimated mean value x=Vm and a standard deviation σv can be obtained (refer to FIG. 8).

b) However, in a case where the distribution profile is disrupted at a portion where the brightness distribution is smaller than x=μ, then Vm falls out of the valid region. In this case, by calculating V1:F(Vm−2.0σv) and V2:F(Vm−1.0σv) existing within the valid region, σv and Vm can be estimated as $$\sigma v = V2 - V1$$

$$Vm = V2 + \sigma v$$

Figure 9:
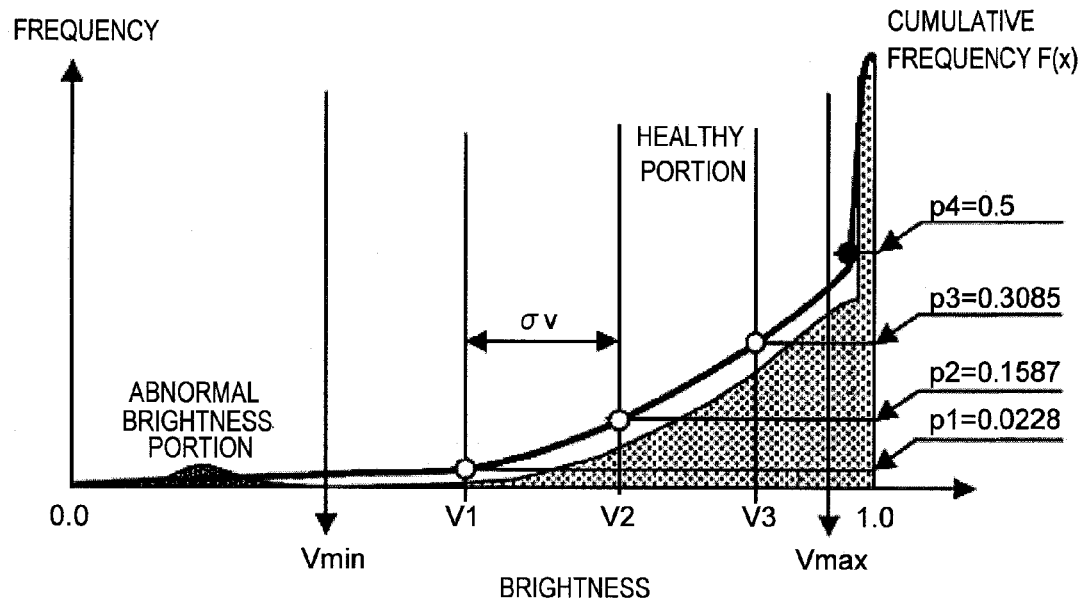
FIG. 9 is an explanatory diagram of estimating a mean value Vm in a case of an abnormal distribution profile according to the present invention.

(refer to FIG. 9).

c) Alternatively, when the abnormal brightness portion becomes relatively large, V1:F(Vm−2.0σv) and V2:F(Vm−1.0σv) fall out of the valid region. In this case, from brightness values V3:F(Vm−0.5σ)=0.3085 and Vm:F(Vm)=0.5 existing within the valid region, σv can be expressed as σv=(Vm−V3)×2, thereby enabling σv and Vm to be estimated (refer to FIG. 10).

By using this method, a mean value and a standard deviation of a healthy portion can be obtained without having to use lumber to become a reference and regardless of the distribution profile. When using lumber to become a reference, a mean value and a standard deviation thereof are to be used without performing calculations.

7) Next, in order to calculate an actual area of a defective portion, only color pixels deviating from standard in the color distribution space whose original lumber pixel g[x, y] locally forms a cluster must be selected. In doing so, a method referred to as relaxation that is a general image processing technique can be used to remove discontinuous isolated points and enhance portions with significant deviation while taking the colors of surrounding pixels into consideration.

As an example, a defective area due to abnormal chromaticity and brightness can be determined by relaxation that uses a total deviation value Zt[x, y] of chromaticity and brightness as an initial label (refer to the description of FIG. 4).

Previously, in automatic quality inspection of lumber, defective portions have been detected based solely on light-dark of the surface color or by specifying a particular color. However, such methods are unable to accommodate changes in bright portions and in color, resulting in all inspection objects being judged nondefective.

Among the surface colors of lumber, portions that seem unpleasant to the human eye and which affect quality are likely to be in colors that do not occur naturally in lumber. Such colors appear as a difference in the color distribution in a three-dimensional color space. Defective portions can now be detected with high accuracy by a unified method in which such differences are separated and detected.

In addition, since fungi and the like which affect lumber quality have different colors depending on the type or the area of production of lumber, it is difficult to detect all such fungi with high accuracy using a single method. However, according to the present invention, even if types of lumber to become inspection objects differ, detection can be performed without hardly varying reference central axis coordinate values. Even if detection accuracy deteriorates according to species, detection accuracy can be restored simply by varying the reference central axis coordinates of the three-dimensional color distribution which is an initial value.

Furthermore, while pitch, bark, and the like have been difficult to detect by an appearance inspection using image processing, pitch, bark, and the like can now be detected.

Since blackened portions of bark and the like can now be detected with high accuracy, judgment of a live knot and a dead knot can be readily made by judging whether a blackened bark remains or not.

(6) Description of Relaxation

FIG. 4 is an explanatory diagram of relaxation. Hereinafter, a description will be given on processes S1 to S3 shown in FIG. 4.

In the processes, a defect probability Pi(x, y) is set for each pixel g(x, y) in the image to become an inspection object, where Pi(x, y) is a defect probability of the pixel g(x, y) after an ith iteration.

S1: The image processor assigns an initial probability P0 (x, y) (0 to 1.0) to each pixel g(x, y) in the image to become an inspection object, and proceeds to process S2. In process S1, P0(x, y) is set as follows using a color deviation value Z(x, y).

$$P0(x,y) = Z(x,y) : 0 < Z < 1.0$$

1.0: Z ≧ 1.0

S2: For all pixels,
if (0.0<Pi(x, y)<1.0),
then the image processor calculates a probability mean value <P> of neighboring pixels of Pi(x, y)
updates the probability by Pi+1=Pi+α(<P>−Pi) (where α is an influence coefficient of neighboring pixels which ranges from around 1 to 4),
and proceeds to process S3.

If (Pi(x, y)≦0.0 or Pi(x, y)≧1.0), then the image processor assumes that $$Pi+1 = Pi$$

and proceeds to process S3 without updating probability.

S3: The image processor examines a convergence condition.

If, for Pi(x, y),
the number of iterations I is greater than a specified number (I>specified number), and
the percentage of the number of pixels of Pi=0.0 and pi=1.0 among all pixels is greater than a specified percentage (>specified percentage), then the process is terminated.

If not, process S2 is repeated.

In this case, the specified number of iterations is set to around 10 and the specified percentage of the number of pixels of Pi=0.0 and pi=1.0 among all pixels is set to around 99%.

(7) Description of Color Distribution in HSV Color Space

Figure 5:
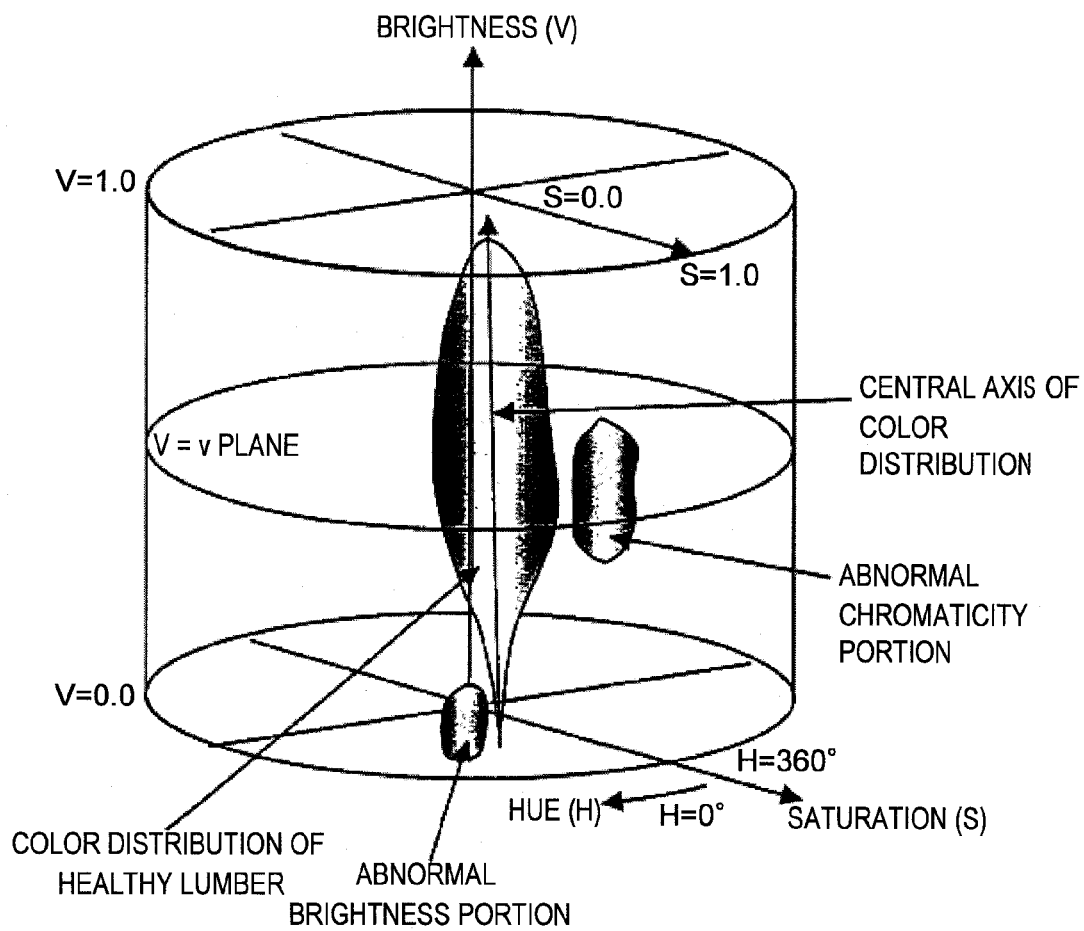
FIG. 5 is an explanatory diagram of a color distribution in an HSC color space according to the present invention.

FIG. 5 is an explanatory diagram of a color distribution in an HSV color space. In FIG. 5, the upward direction represents brightness (V: in this case, V=0.0 to 1.0), the diametrical direction in the same brightness plane represents saturation (S: in this case, S=0.0 to 1.0), and the circumferential direction in the same brightness plane represents hue (H: in this case, H=0° to 360°). A color distribution of healthy lumber includes significant upper and lower color distribution regions. A central axis (reference central axis) of the color distribution is indicated by the upward arrow.

In addition, a color distribution of an abnormal chromaticity portion that is a discolored portion such as fungi is shown on the right-hand side as an abnormal chromaticity region. Furthermore, an abnormal brightness portion such as a burn caused by a kiln or the like is shown towards the bottom as a small color distribution region.

(8) Description of Pixel Distribution in Specific Brightness Plane

Figure 6:
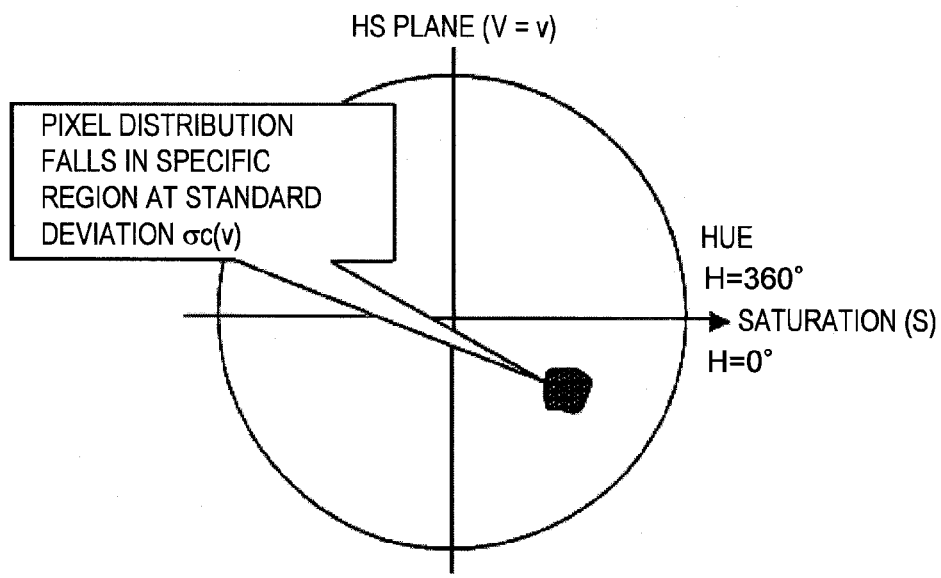
FIG. 6 is an explanatory diagram of a pixel distribution on a specific brightness v plane according to the present invention.

FIG. 6 is an explanatory diagram of a pixel distribution on a specific brightness v plane. FIG. 6 shows a pixel distribution of an abnormal chromaticity portion in a specific brightness v plane. In this case, the pixel distribution of an abnormal chromaticity portion ranges in a specific region (refer to hatched portion) at a standard deviation σc(v).

(9) Description of Pixel Distribution in Central Axis Direction

Figure 7:
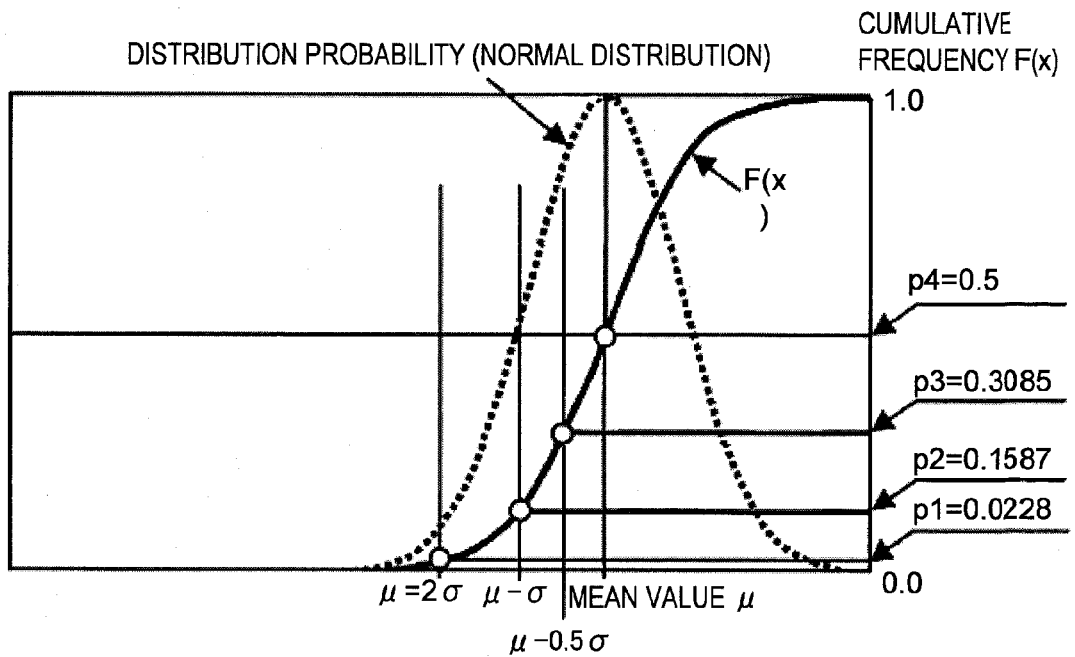
FIG. 7 is an explanatory diagram of a cumulative frequency F(x) of normal distribution according to the present invention.

FIG. 7 is an explanatory diagram of a cumulative frequency F(x) of normal distribution. In FIG. 7, a general normal distribution (distribution probability) is indicated by the dotted line, and a cumulative frequency (cumulative probability distribution function) F(x) is a normalization performed by dividing an integrated value of the healthy portion of lumber by the total number of pixels N. In this case, p1=0.0228 (μ−2σ), p2=0.1587 (μ−1.0σ), p3=0.3085 (μ−0.5σ), and p4=0.5 (mean value=μ).

FIG. 8 is an explanatory diagram of a pixel distribution (normal distribution profile) in a central axis direction. FIG. 8 shows a histogram in the reference central axis (brightness axis) direction of a three-dimensional color distribution. In the brightness histogram, let brightnesses corresponding to p1, p2, p3, and p4 described above be V1, V2, V3, and Vm, respectively, and valid regions attainable by the healthy portion of the lumber surface be Vmin and Vmax. In the case of the diagram, if a brightness position corresponding to V2:F(Vm−σ)=0.1587 and Vm:F(Vm)=0.5 existing in the valid region can be found, then an estimated mean value x=Vm and a standard deviation σv can be obtained.

FIG. 9 is an explanatory diagram of estimating a mean value Vm in a case of an abnormal distribution profile. FIG. 9 shows a histogram in the reference central axis (brightness axis) direction of a three-dimensional color distribution. With this brightness histogram, in a case where the distribution profile is disrupted at a portion where the brightness distribution of the healthy portion of the lumber surface is smaller than x=μ, then Vm falls out of the valid region. In this case, σv and Vm can be estimated by calculating V1: F(Vm−2.0σv) and V2: F(Vm−1.0σv) and from σv=V2−V1 and Vm=V2+σv.

Figure 10:
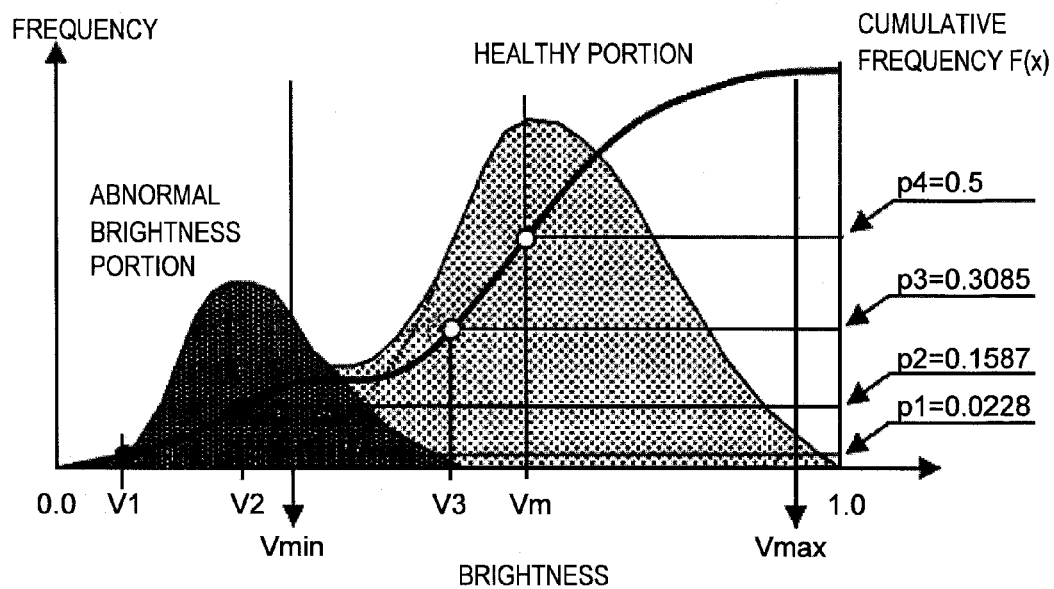
FIG. 10 is an explanatory diagram of a case where an abnormal brightness portion occupies a large area according to the present invention.

FIG. 10 is an explanatory diagram of a case where an abnormal brightness portion occupies a large area. FIG. 10 shows a histogram in the reference central axis (brightness axis) direction of a three-dimensional color distribution. With this brightness histogram, in a case where the area of the abnormal brightness portion of the lumber surface becomes relatively large, then V1: F(Vm−2.0σv) and V2: F(Vm−1.0σv) fall out of the valid region. In this case, from brightness values V3: F(Vm−0.5σ)=0.3085 and Vm: F(Vm)=0.5 existing within the valid region, σv can be expressed as σv=(Vm−V3)×2, thereby enabling σv and Vm to be estimated.

As shown, when the brightness histogram does not form a normal distribution due to camera characteristics or the like (for example, when sensor sensitivity characteristics are non-linear at a portion close to 1.0 brightness), the mean value Vm and the standard deviation σv may not necessarily be obtained accurately. However, even in such a case, by assuming that the histogram follows a standard normal distribution, an entire distribution can be estimated from the histogram at the slope of the distribution (two points), and the mean value Vm and the standard deviation σv can be obtained.

Accordingly, a mean value Vm and a standard deviation σv of a healthy portion can be obtained (estimated) by an image processor using two points among points V1 to Vm existing within a valid region (Vmin to Vmax). As an order of priority of the two points to be used, a mean value Vm and another point (one point among V1 to V3) are to be used first, and two points among V1 to V3 are to be used if the mean value Vm does not exist within the valid region.

(10) Description of Program Installation

The image processor (image processing means) 1, the sorter controller (sorter controlling means) 2, the camera image acquisition boards 11a, 11b, and 11c, the main computer 14, and the like can be configured by a program to be executed by the main processing unit (CPU) and stored in a main storage. The program is to be processed by a computer. The computer is made up of hardware such as a main control unit, a main storage, a file device, an output device such as a display, and an input device.

The program according to the present invention is installed onto this computer. Installation is performed by storing, in advance, the program onto a portable recording (storage) medium such as a floppy or a magnetic optical disk and the like, and installing the storage medium into a file device included in the computer either via a drive device provided on the computer to enable access to the storage medium or via a network such as a LAN. Accordingly, a lumber inspection device capable of accurately detecting, using color distribution, defective portions due to discoloration of the lumber surface which affect lumber quality can be readily provided.

The present invention has the following advantageous effects.

(1) Image processing means obtains a color distribution of a color image captured by imaging means, compares the obtained color distribution with a predetermined color distribution of normal lumber, judges the obtained color distribution as an abnormal one when it is deviated from the color distribution of normal lumber by a predetermined value or more, and detects an area on the surface of the lumber captured by the imaging means whose abnormal color distribution has a value greater than the predetermined value as a defect of the lumber. Therefore, defective portions due to discoloration of the lumber surface which affect lumber quality can be accurately detected using color distribution.

(2) When setting, as an inspection object, lumber whose defective area is small relative to an inspection object area, image distributions acquired on a per-inspection object basis are replaceably used from case to case as predetermined color distributions of normal lumber. Therefore, predetermined color distributions of normal lumber can be readily acquired.

(3) Since an abnormal brightness portion is detected by obtaining a brightness histogram of a color distribution of a captured color image, an abnormal brightness portion such as a burn can be readily detected.

(4) The entire brightness histogram of the predetermined color distribution of normal lumber is assumed so as to follow a normal distribution and an entire normal distribution is estimated from a cumulative frequency of a partial region. Therefore, a color distribution of normal lumber can be estimated from lumber to be inspected without having to determine, in advance, a color distribution of normal lumber.

The object and advantage of the present invention will be realized and attained by means of the elements and combinations particularly pointed out in the claims. It is to be understood that both the foregoing general description and the following detailed description are exemplary and explanatory and are not restrictive of the invention, as claimed.

All examples and conditional language recited herein are intended for pedagogical purposes to aid the reader in understanding the invention and the concepts contributed by the inventor to furthering the art, and to be construed as being without limitation to such specifically recited examples and conditions, nor does the organization of such examples in the specification relate to a showing of the superiority and inferiority of the invention. Although the embodiment(s) of the present invention have been described in detail, it should be understood that the various changes, substitutions, and alterations could be made hereto without departing from the spirit and scope of the invention.

The invention claimed is:

1. A lumber inspection method executed by a programmed processor, comprising:
   obtaining a color image of lumber captured by imaging means;
   obtaining a color distribution of the color image captured by the imaging means;
   comparing the obtained color distribution with a predetermined color distribution of normal lumber;
   judging the obtained color distribution as an abnormal one when it is deviated from the color distribution of normal lumber by a predetermined value or more; and
   detecting an area on the surface of the lumber captured by the imaging means whose abnormal color distribution has a value greater than the predetermined value as a defect of the lumber.

2. The lumber inspection method according to claim 1, wherein when setting, as an inspection object, lumber whose defective area is small relative to an inspection object area, image distributions acquired on a per-inspection object basis are replaceably used from case to case as the predetermined color distributions of normal lumber.

3. The lumber inspection method according to claim 1, wherein an abnormal brightness portion is detected by obtaining a brightness histogram of the color distribution of the captured color image.

4. The lumber inspection method according to claim 3, characterized in that, for the brightness histogram of the color distribution of normal lumber determined in advance, an entire normal distribution is estimated from a cumulative frequency of a partial region on the assumption that an entire distribution follows a normal distribution.

5. The lumber inspection method according to claim 2, wherein an abnormal brightness portion is detected by obtaining a brightness histogram of the color distribution of the captured color image.

6. A lumber inspection device comprising:
   an imaging unit for capturing a color image of lumber; and
   an image processing unit for obtaining a color distribution of the color image captured by the imaging unit, comparing the obtained color distribution with a predetermined color distribution of normal lumber, judging the obtained color distribution as an abnormal one when it is deviated from the color distribution of normal lumber by a predetermined value or more, and detecting an area on the surface of the lumber captured by the imaging unit whose abnormal color distribution has a value greater than the predetermined value as a defect of the lumber.

7. The lumber inspection device according to claim 6, wherein when setting, as an inspection object, lumber whose defective area is small relative to an inspection object area, the image processing unit replaceably uses image distributions acquired on a per-inspection object basis from case to case as the predetermined color distributions of normal lumber.

8. The lumber inspection device according to claim 6, wherein the image processing unit detects an abnormal brightness portion by obtaining a brightness histogram of the color distribution of the captured color image.

9. The lumber inspection device according to claim 8, wherein, for the brightness histogram, the image processing unit estimates an entire normal distribution from a cumulative frequency of a partial region on the assumption that an entire distribution follows a normal distribution.

10. The lumber inspection device according to claim 7, wherein the image processing unit detects an abnormal brightness portion by obtaining a brightness histogram of the color distribution of the captured color image.

11. A computer-readable storage device storing a program for causing a computer to function as:
   an imaging unit for capturing a color image of lumber; and
   an image processing unit for obtaining a color distribution of the color image captured by the imaging unit, comparing the obtained color distribution with a predetermined color distribution of normal lumber, judging the obtained color distribution as an abnormal one when it is deviated from the color distribution of normal lumber by a predetermined value or more, and detecting an area on the surface of the lumber captured by the imaging unit whose abnormal color distribution has a value greater than the predetermined value as a defect of the lumber.

* * * * *